US011000450B2

(12) United States Patent
Wu et al.

(10) Patent No.: US 11,000,450 B2
(45) Date of Patent: May 11, 2021

(54) COLLAPSIBLE NASAL EJECTING CATHETER

(71) Applicants: Lih-Chiu Wu, Kaohsiung (CN); Hui-Shuan Lee, Kaohsiung (CN); Tsang-Mu Lee, Kaohsiung (CN); Tze-Yu Lee, Kaohsiung (CN)

(72) Inventors: Lih-Chiu Wu, Kaohsiung (CN); Hui-Shuan Lee, Kaohsiung (CN); Tsang-Mu Lee, Kaohsiung (CN); Tze-Yu Lee, Kaohsiung (CN)

( * ) Notice: Subject to any disclaimer, the term of this patent is extended or adjusted under 35 U.S.C. 154(b) by 94 days.

(21) Appl. No.: 16/349,427

(22) PCT Filed: Dec. 25, 2017

(86) PCT No.: PCT/CN2017/118170
§ 371 (c)(1),
(2) Date: May 13, 2019

(87) PCT Pub. No.: WO2018/121459
PCT Pub. Date: Jul. 5, 2018

(65) Prior Publication Data
US 2019/0282443 A1  Sep. 19, 2019

(30) Foreign Application Priority Data
Dec. 26, 2016 (WO) ............... PCT/CN2016/112048

(51) Int. Cl.
*A61H 35/04* (2006.01)
*A61M 3/02* (2006.01)
*A61M 25/00* (2006.01)

(52) U.S. Cl.
CPC .......... *A61H 35/04* (2013.01); *A61M 3/0279* (2013.01); *A61M 25/007* (2013.01); *A61H 2205/023* (2013.01); *A61M 2210/0618* (2013.01)

(58) Field of Classification Search
CPC .............. A61H 35/04; A61H 2205/023; A61H 2201/0173; A61H 2201/1253;
(Continued)

(56) References Cited

U.S. PATENT DOCUMENTS 6,536,437 B1 * 3/2003 Dragisic ............... A61M 16/04
128/207.18
2007/0250105 A1 * 10/2007 Ressemann ...... A61B 17/12104
606/196

(Continued)

FOREIGN PATENT DOCUMENTS

CN  10-3565634 A  2/2014
CN  20 4501596 U  7/2015
(Continued)

OTHER PUBLICATIONS

International Search Report dated Mar. 23, 2018, in corresponding International Application No. PCT/CN2017/118170.

*Primary Examiner* — Bhisma Mehta
*Assistant Examiner* — Rachel T. Smith
(74) *Attorney, Agent, or Firm* — Bacon & Thomas, PLLC

(57) ABSTRACT

A catheter, including a catheter body and a connector, can be adapted to a syringe for nasal flushing treatment. The catheter body is made of a soft material and has a flat closed distal end, a transitional segment having a flat closed segment and a lumen-containing oval segment, a circular normal segment and an open end on the opposite side of the flat closed distal end as well as multiple side-holes disposed near the closed end so that the catheter can be operated by patient to insert into a slit space of nasal cavity smaller than the diameter of the circular normal segment.

4 Claims, 12 Drawing Sheets

(58) Field of Classification Search
CPC .............. A61M 3/0279; A61M 25/007; A61M 2210/0618; A61M 2025/0025; A61M 3/0262; A61M 2210/0681; A61M 25/0054; A61M 31/00; A61M 16/0461; A61M 16/0666; A61M 25/00; A61M 25/02; A61M 2025/0226; A61M 15/08; A61M 3/00; A61M 2021/0016; A61M 25/0023; A61M 25/0032; A61M 2025/0035; A61M 2100/0618; A61L 9/14; B05B 11/00; A61F 9/0008; A61F 5/08; A62B 23/06; A61B 17/12022

See application file for complete search history.

(56) References Cited

U.S. PATENT DOCUMENTS

2014/0214048 A1* 7/2014 Gulcher .............. A61M 25/003
  606/127
2020/0269011 A1* 8/2020 Carlsson .............. A61M 25/007

FOREIGN PATENT DOCUMENTS

| EP | 2687250 A2 | 1/2014 |
| JP | 2009-072581 A | 4/2009 |
| TW | 2016-13661 A | 4/2016 |
| TW | 2017-35955 A | 10/2017 |
| WO | 2017-063152 A1 | 4/2017 |

* cited by examiner a-a a-a b-b b-b c-c d-d

COLLAPSIBLE NASAL EJECTING CATHETER

BACKGROUND OF THE INVENTION

1. Field of the Invention

The present invention relates to a nasal flushing catheter, and more particularly to a collapsible nasal ejecting catheter for cleaning the mucus and crust deeply within the nasal cavity and nasopharynx to improve the symptoms of chronic sinusitis.

2. Description of the Related Art

Despite not being life-threatening, the chronic sinusitis by the diagnostic criteria of symptoms lasting more than 12 weeks is a troubling disease. Currently, there is no cure for the disease. The main symptoms of nasal obstruction, foreign body sensation in the throat and cough would bother the patient relentlessly and may even last for life-long. Antibiotics are only used for control of acute infection, and surgical operation is a method to remove the obstruction or to restore the patency of sinus orifice to prevent acute episode of sinusitis. No matter what the treatment is taken, the disease remains unchanged, and the symptoms persist. Hence, otolaryngologists recommend long-term home-remedy of nasal flushing treatment at least twice a day.

FIG. 1 and FIG. 2 are the sagittal section view and the coronal section view of the human nasal cavity. The coronal section view of the nasal cavity shows a triangle configuration. The nasal cavity is divided into two spaces by the nasal septum. In each space, the nasal cavity proper located between the hollow nasal vestibule 90 anteriorly and the nasopharynx 91 posteriorly, is divided into three slightly curved slit-like passages as well as a para-septal space by three pieces of curved plate-like structure. The said three curved plate-like structures are called the superior turbinate A, the middle turbinate B, as well as the inferior turbinate C, and the said three curved slit-like passages are called the superior nasal meatus A1, the middle nasal meatus B1 and the inferior nasal meatus C1. The middle nasal meatus is further divided into a 2 cm long descending section (B1D) and a 1 cm long horizontal section (B1H). The para-septal space can be divided into the superior para-septal space D1, the middle para-septal space D2 and the inferior para-septal space D3 by the lower edge of the superior turbinate A, the middle turbinate B, as well as the lower turbinate C. The anteroposterior distance of the nasal cavity is about 5 cm; the middle turbinate B and the inferior turbinate C, as well as the middle nasal meatus B1 and the inferior nasal meatus C1 are also 5 cm in length. The superior turbinate A and the superior nasal meatus A1 only present in the posterior half of the nasal cavity, and their anterior-posterior distance is about 2.5 cm. All the three turbinates, the nasal septum and the side wall of nasal cavity are constituted by bones and covered by mucosa to increase the surface area to ensure two functions: 1. Adjusting the humidity and temperature of inspired air. 2. Filtering the particulate substance in the air to avoid falling into the trachea and lungs (please see nasal cavity by Wikipedia). These three nasal passages communicate with each other with the para-septal space medially, and the nasal vestibule 90 anteriorly and the nasopharynx 91 posteriorly. All the mucus secreted from four pairs of sinuses located on both sides and superior aspect of nasal cavity, are discharged from the sinus orifices (usually of 1 mm or less) located at the roofs of the superior nasal meatus A1, the middle nasal meatus B1 and the nasopharynx. When the diagnosis of chronic sinusitis is confirmed, most patients already have severe symptoms and cannot recover to the natural conditions. Hence, it is difficult to remember when and how the disease occurred; however, its pathophysiology can be illuminated by the natural course of common cold.

The nasal secretions can be understood through a cold process. Running nose occurs in the early stage. The nasal discharge at this stage is a kind of clear liquid without mucus and can be completely evaporated. Afterwards, the discharge becomes slightly viscous but easy to expel. Then, the secretion becomes difficult to expel. Afterwards, the secretion becomes jelly-like scab, and finally solid booger (crust) which is similar to that excavated from the nasal vestibule 90. There are four states of secretion. The symptoms of chronic sinusitis are due to accumulation of these mucus and booger within the nasal cavity proper. The symptoms of common cold rarely last more than 4 weeks, while the symptoms of chronic sinusitis persist much longer. Only chronic sinusitis has symptoms persisting more than 12 weeks, therefore, can be used as a diagnostic criteria. If no other obstructive causes such as polyps or tumors present, the diagnosis can be confirmed. The allergic rhinitis or hay fever so on may also present with severe nasal obstruction persisting for a long time, but is always accompanied by a lot of watery nasal discharge and absence of foreign body sensation in the throat. As long as the allergen disappears, the symptoms disappear. In addition, allergic rhinitis is a periodic or seasonal disease, while chronic sinusitis is a life-long persisting disease.

Because the secretions of chronic sinusitis are too sticky, when discharged to nasal cavity (meatus), it is difficult to remove completely from the nasal cavity either by blowing nose or by snorting. Mucus is easy to stick to a narrow space to cause local obstruction, which allows no air to pass through and thus mucus maintains a liquid state. However, if gravity exceeds adhesion, mucus flows forward or downward to a wider space depending on patient's position. If the mucus moves forward to nasal vestibule 90, it is known as nasal mucus and could be further dried to become booger. The mucus may also move backward to the nasopharynx 91, known as post-nasal drip, and it is difficult to clean by suctioning or swallowing. The mucus that has not been removed and stays in the nasal cavity does not evaporate like watery nasal discharge, and if it moves into a larger space, it becomes a thin layer. Since the thin layer mucus does not cause complete obstruction, the mucus will be dried by respiratory air to reduce the volume. It will stick to nasal cavity layer by layer, then spreads out from the sinus orifice of the middle nasal meatus B1 and the superior nasal meatus A1, and finally it will cause persistent and severe nasal obstruction. The mucus continuously discharges from the opening of the superior nasal meatus and the middle nasal meatus, and spreads from the top to down. Thus, a suspended conglomerated mass on the upper part of nasal is created. The lowest part of mucus still contacts with the respiratory air, and becomes a hard crust. The mucus migrating to nasopharynx has the same outcome as that in the nasal cavity undergoing repeated drying and coating process. Because the nasopharynx 91 is a wide top-down respiratory tract, the mucus will be dried faster. Both the liquid mucus and solid booger may fall downward and have the possibility to fall into the trachea to cause foreign body sensation in the throat and initiate a defense mechanism of cough. The foreign body sensation in the throat and cough is also a great suffering, and may even restrain the social activities of patient. The symptoms of nasal obstruction, foreign body sensation in the throat and cough may also affect the sleeping quality resulting in poor quality of life and poor working performance. Finally, if these symptoms are ignored, the mucus as well as the crust will eventually block the orifice of the paranasal sinus. This will result in the accumulation of mucus in the paranasal sinus to cause acute sinusitis. Acute sinusitis is a serious disease required vigorous medical and/or surgical treatment. Even the acute episode is controlled; the disease process and the symptoms remain the same.

The interchange of mucus, jelly-like scab and solid booger (crust) can be observed in in-vitro experiments. The mucus exposed in the air will become jelly-like scab, and the jelly-like scab will become solid booger. The volume may shrink more than 10 times from liquid mucus to solid booger. The interchange duration depends on the degree of humidity and the air circulation. Reversely, if the solid booger is soaked in the water for one hour, it will become half-solid scab, and then it gradually becomes mucus. Therefore, the nasal flushing treatment as an auxiliary treatment for chronic sinusitis sounds rather reasonable. However, as FIGS. 1, 2 and 3 show, the nasal cavity is a complex slit-like structure composed of three nasal passages and a para-septal space, rather than a hollow empty space. The nasal cavity can communicate with outside of the body through the nasal vestibule 90, or communicate with outside of the body through the nasopharynx and oral cavity. It is a unique open space in the human body, because both its front and rear ends connect to the outside the body (the oral cavity is also an open space, but the muscle group can move voluntarily, so it is a hollow space that can be opened and closed). The flushing fluid delivered from the outside will leak immediately from the front and rear ends. Because of the impediment of turbinates, the entire nasal cavity cannot be filled up by any posture. Further, moistening mucus does not mean mucus cleansing; cleansing is much more difficult than moistening.

We further conduct the following experiment to simulate the mechanism of flushing the nasal cavity: using horizontal spouts to flush upright plastic plates stuck with mucus, jelly-like scab or booger, and the strengths of spouts are classified by the vertical height as follows: low-pressure spouts under 45 cm vertical height, medium-pressure spouts between 45 to 90 cm vertical height and high-pressure spouts over 90 cm vertical height. The results were observed as follows: the low-pressure spouts let the mucus become thin nasal discharge, and also let the jelly-like scab become mucus, but it cannot change the solid booger; the medium-pressure spouts let the mucus and jelly-like scab become liquid nasal discharge, and also let the solid booger become thick mucus; high-pressure spouts let the solid booger fall off, and jelly-like scab and mucus are easily be flushed away. Therefore, the flushing efficiency is relevant to the vertical height of the spouts.

Please refer to FIGS. 4 and 5, Taiwan Invention Patent No. I542371, the applicant's prior application (hereinafter "prior application"), its objective is to improve the prior nasal flushing catheter, Invention Patent No. I515025. The improvement is as follows: 1. using the total area of the side-holes to control the vertical height of the spouts and classified the catheter 611 by vertical height of spouts as high pressure, medium pressure, and low pressure. The high-pressure catheter 611 must be a larger pressure-tolerant catheter 611, which can remove most of the crust and mucus to improve the symptoms of nasal obstruction. Although it can improve the prior application, it cannot reach the deep narrow recess. Despite the thinner and multiple small spouts have more chances to flush the slit-like space, but the effect is still not satisfactory, the reason we believe is that the large catheter fails to reach deeply within the narrow slit-like space, where can only be flushed by strong spouts parallel to the slit-like space, but the perpendicular vector of these parallel spouts rapidly decreases as the distance increases, so its function is still inferior to the microcatheter that can reach deep recess. 2. The retained stylet 8 within the catheter to improve the controllability of the microcatheter, but the weak spouts of microcatheter 611 only has weak efficiency. Further, it is not easy to manufacture a catheter of 1 mm outer diameter, but the narrow portion of nasal cavity of the severe patient may be even as narrow as 0.5 mm, which is difficult for insertion even by a microcatheter 611. The microcatheter also has the risk of accidental insertion into the sinus. In addition, according to experience of relatives and friends, although the nasal obstruction can be improved immediately, but the foreign body sensation in the throat and cough still cannot be improved to the desired condition. Further, both the large and small catheters must be used in combination. At last, it is also inconvenient to measure the width of the middle and superior nasal meatus by computed tomography for selecting the appropriate catheters. Therefore, further improvement is desired.

Those mentioned above is our unpublished personal experience, which cannot be conceived groundless, especially the chance of accidental insertion into the sinus by patients. For other people, before the filing date of the present invention, no one would study this case without patent in hand, even though one may study hard, but the prior application sounds very reasonable and it is difficult to find the disadvantages. Further if the prior application is regarded as an ineffective treatment, it also proves that the consensus of medical experts all over the world makes sense (Wikipedia, key word: chronic sinusitis, Medscape Reference; Wikipedia, keyword: chronic sinusitis Mayo Clinic; Wikipedia, keyword: sinusitis, University of Maryland Medical Center-sinusitis, page 11-12): When the nasal flushing treatment is ineffective, it is necessary to consider the suggestion of surgical operation. It is difficult to get rid of the authoritative influence of medical experts. In addition, the prior application has not been commercialized, and it is impossible to undergo human subject research. Thus, it is impossible to find the disadvantages of the prior application. Therefore, we have duty to improve the case for the benefit of patients. Because we have three roles as physicians, patients, and persons skilled in the art, the invention can be completed after two years of continuous experiment among friends and relatives.

Technical Problem

The technical problem to be solved is the inconvenience of operation of the prior invention.

SUMMARY OF THE INVENTION

Therefore, the purpose of the present invention is to provide an effective and easy handling catheter, especially to provide a multiple-function catheter having stronger spouts and easy insertion into the deep narrow slit-like space, and should not insert into sinus accidentally.

A collapsible nasal ejecting catheter can be adapted to a syringe for flushing the nasal cavity and nasopharynx, comprises a catheter body and a connector. The catheter includes a flat closed distal end, a transitional segment starting from the closed distal end to a circular appearance, a normal segment having a circular appearance, an open end on the opposite side of the flat closed distal end, and multiple side-holes near the closed end. The catheter body is made of thermoplastic elastomer or other soft and elastic materials can be operated by the patients to insert into their nasal cavity and nasopharynx. The minimum wall thickness of the catheter is not larger than 0.45 mm, and the maximum width of the transitional segment is not less than 1 mm.

Another technique of an embodiment of the present invention is that the maximum width of the flat closed distal end is larger than the minimum diameter of the catheter body.

Another technique of an embodiment of the present invention is that the hardness of the catheter is below 80 Shore A, and the wall thickness of the catheter is not larger than 0.45 mm.

Another technique of an embodiment of the present invention is that the hardness of the catheter is between 80 and 90 Shore A, and the wall thickness of the catheter is not larger than 0.40 mm.

Another technique of an embodiment of the present invention is that the hardness of the catheter is above 90 Shore A, and the wall thickness of the catheter is not larger than 0.35 mm.

The advantage of this invention is that the flat closed distal end, transitional segment and collapsibility render the catheter to navigate in the slit-like space, reaching a narrow space much smaller than the catheter to eject stronger spouts for better flushing effect, and also avoiding accidental entry into the sinus.

EXPLANATION FOR ABBREVIATION

Figure 1:
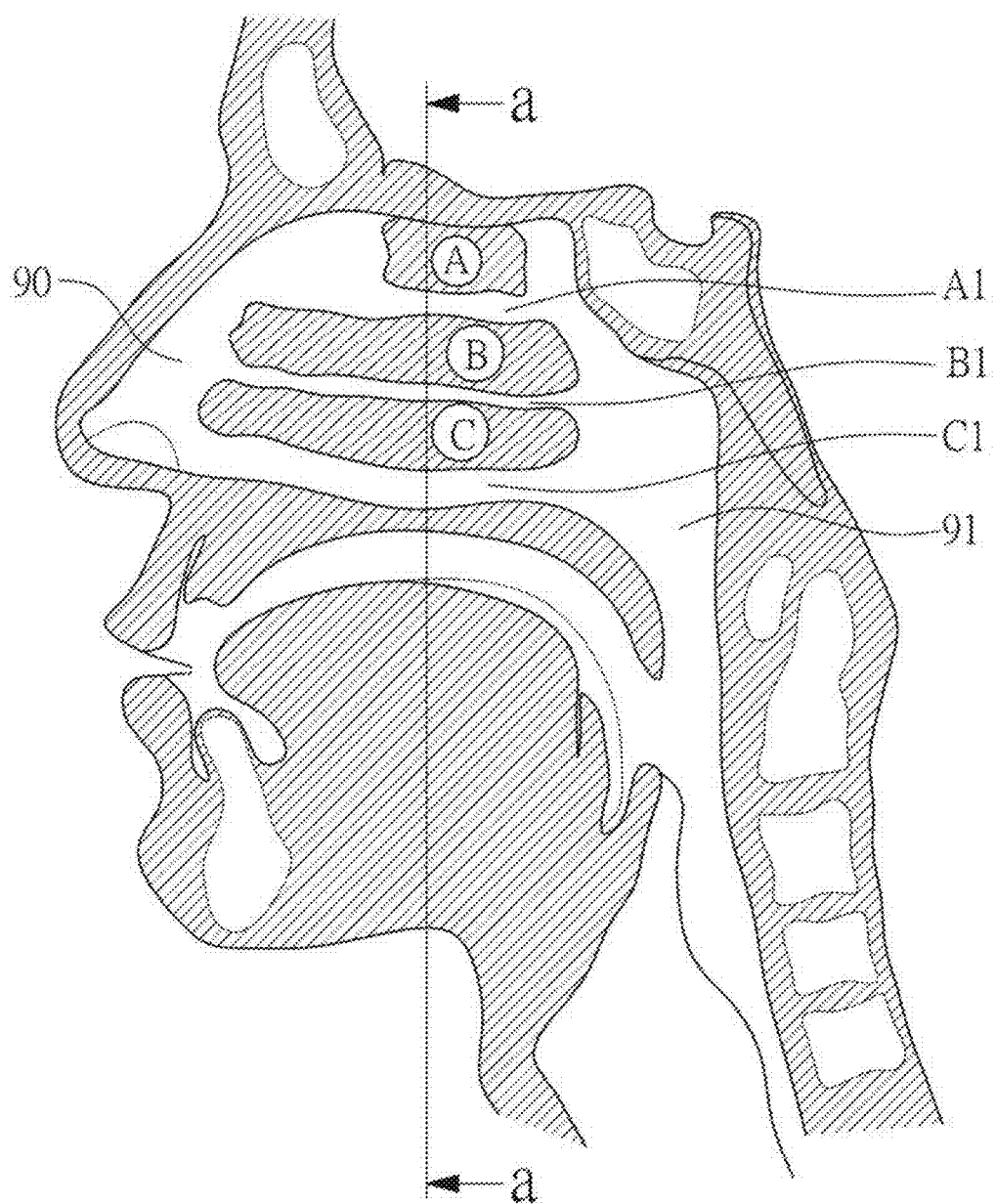
FIG. 1 is a sagittal section view of the human nasal cavity.

B1D descending segment
BH horizontal segment
D para-septal space
D1 superior para-septal space
D2 middle para-septal space
D3 inferior para-septal space
E nasal vestibule
F superior nasal turbinate
F1 superior nasal meatus
FCS flat closed segment
G middle nasal turbinate
G1 middle nasal meatus
H inferior nasal turbinate
H1 inferior nasal meatus
J nasopharynx
LD long axial diameter of oval
NS normal segment
OS oval segment
SD short axial diameter of oval
TAn transitional angle
TS transitional segment
6 nasal ejecting catheter
61 catheter body
611 flat closed distal end
612 open end
613 side-hole
614 catheter wall
615 lumen
62 connector
7 syringe
71 container
72 plunger

DETAILED DESCRIPTION OF THE PREFERRED EMBODIMENTS

The relevant patent features and the technical fields of the present invention will be illuminated by the description of three preferred embodiments in conjunction with the accompanying drawings.

Before explaining the present invention in detail, it is to be understood that similar elements are labeled with the same number. The components and their relationship will be described for elaborating each embodiment firstly, and the detailed parameters, process, and effect will be described later.

Figure 6:
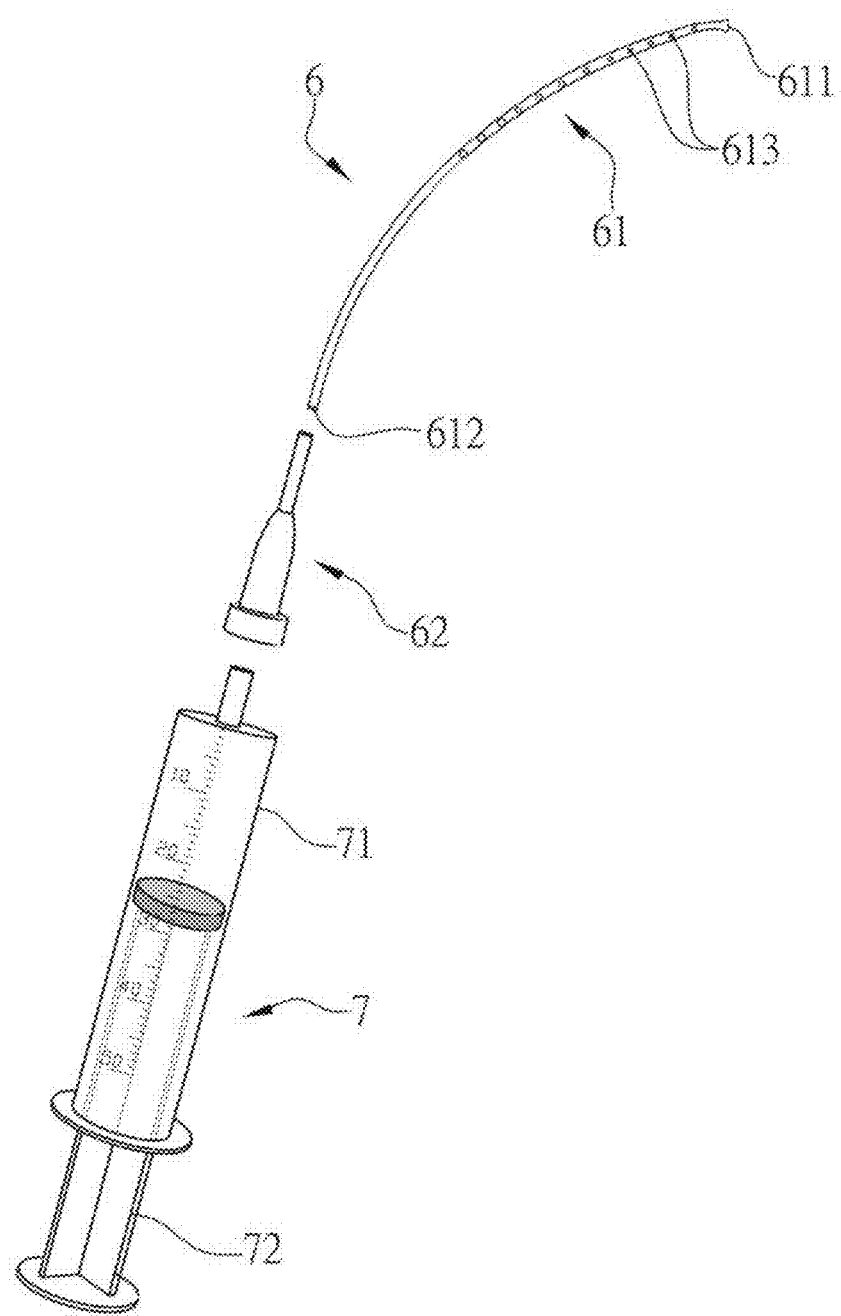
FIG. 6 is an exploded view, showing the components of the present invention.

Please refer to FIG. 6, showing the collapsible nasal ejecting catheter 6, which can be adapted to a syringe 7 for injecting flushing fluid to rinse the nasal cavity and nasopharynx.

The collapsible nasal ejecting catheter 6 includes a catheter body 61 and a connector 62. The catheter body 61 is made of thermoplastic elastomers or other soft and elastic material which can be operated by patient to put into the nasal cavity and nasopharynx. The catheter body 61 has a flat closed distal end 611 and an open end 612 on the opposite side of the flat closed distal end 611. A plurality of side-holes 613 is formed near the flat closed distal end 611.

The syringe 7 is provided with a container 71, and a plunger 72 disposed in the container 71. The container 71 can store liquid, and the plunger 72 can push the liquid in the container 71 to the catheter body 61, so that the fluid is ejected outward through the plurality of side-holes 613 by pressure.

One end of the connector 62 is connected to the open end 612 of the catheter body 61, and the other end is connected to the syringe 7, so that the liquid in the syringe 7 can be delivered to the catheter body 61.

Figure 7:
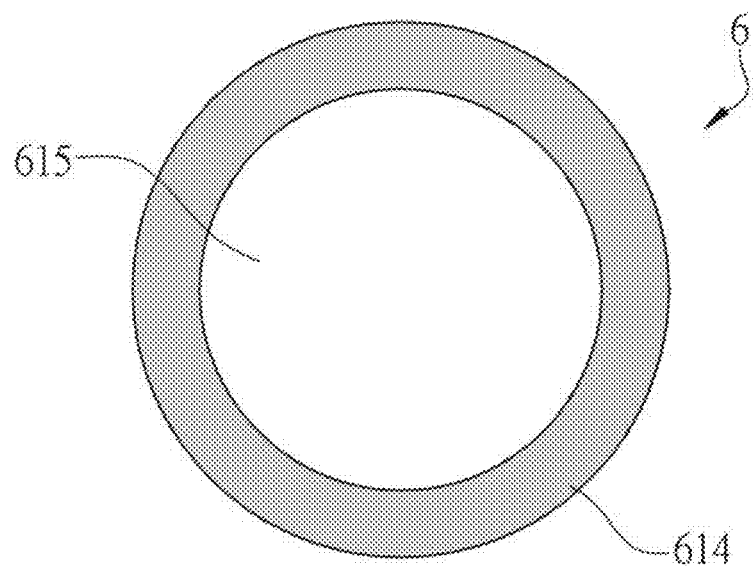
FIG. 7 is a cross-sectional view, showing the present invention under natural condition.
Figure 8:
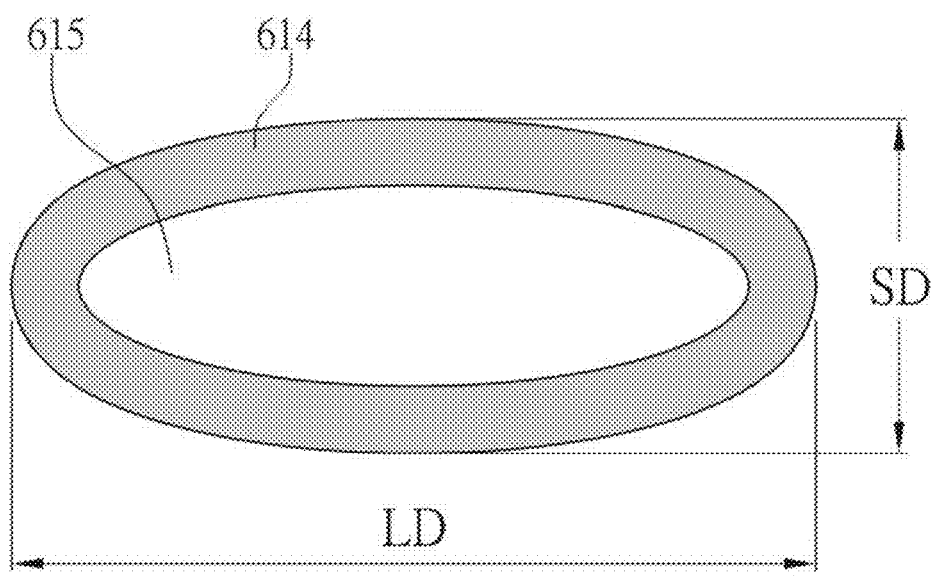
FIG. 8 is a cross-sectional view, showing the present invention under collapsed condition.

Please refer to FIGS. 7 and 8, cross-sectional views of the catheter body 6 under natural and collapsed condition. The catheter body is composed of a catheter wall 614, and a lumen 615 defined by the catheter wall 614, so that it can store liquid and can be a passage of liquid.

The catheter wall 614 is made of soft and elastic material, thus it forms a circle under the natural condition (as shown in FIG. 7). However, after the catheter wall 614 is applied with an external force (not shown in FIGS. 7 and 8), the catheter wall 614 will be collapsed to become oval shape (as shown in FIG. 8).

Figure 13A:
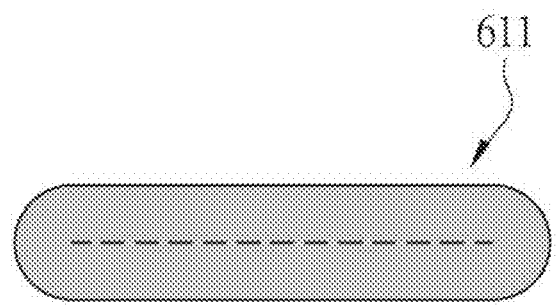
FIG. 13a is a cross-sectional view, showing the b-b line in FIGS. 9 and 10.
Figure 13B:
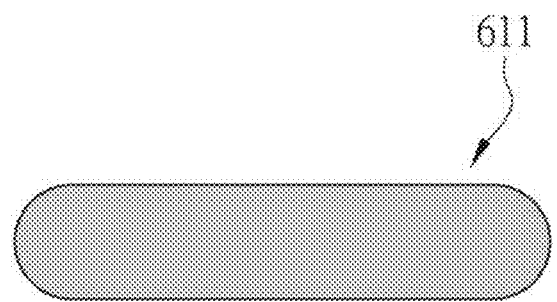
FIG. 13b is a cross-sectional view, showing the b-b line in FIGS. 11 and 12.
Figure 14:
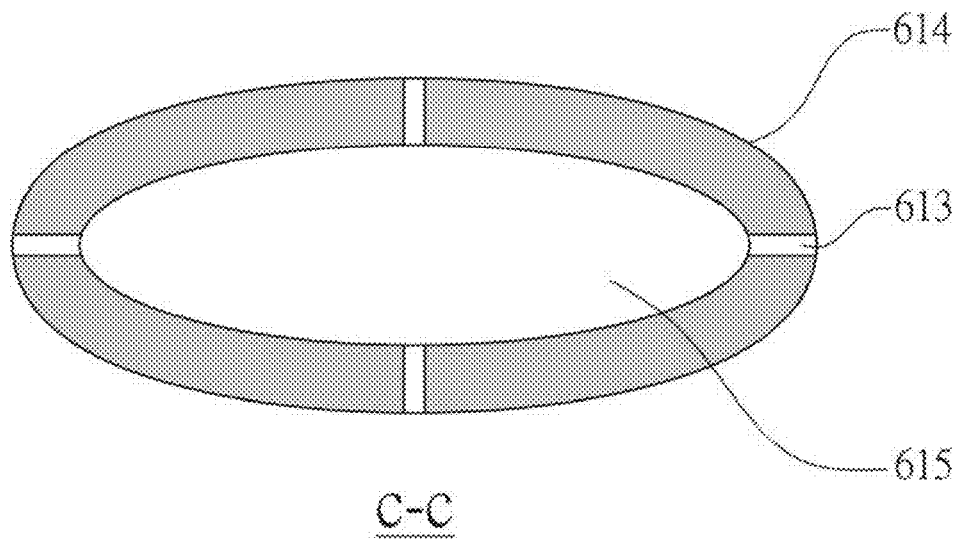
FIG. 14 is a cross-sectional view, showing the c-c line in FIGS. 9, 10, 11, and 12.
Figure 15:
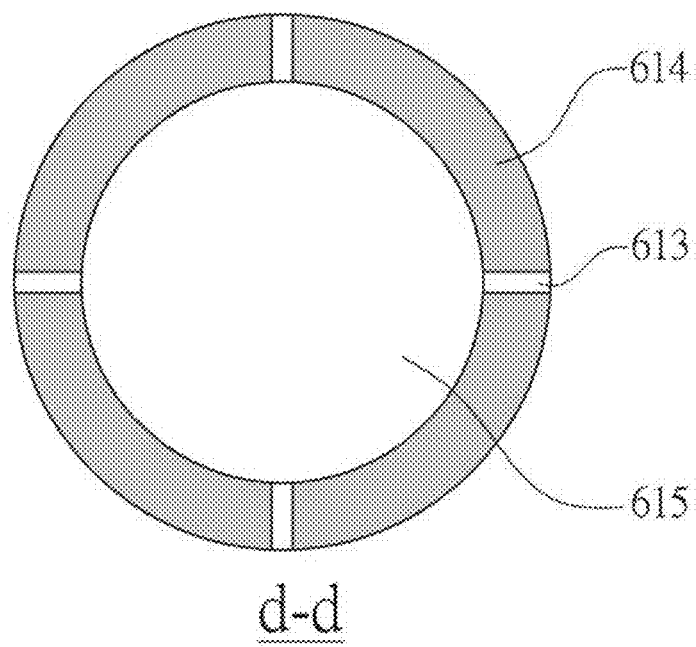
FIG. 15 is a cross-sectional view, showing the d-d line in FIGS. 9, 10, 11, and 12.
Figure 16:
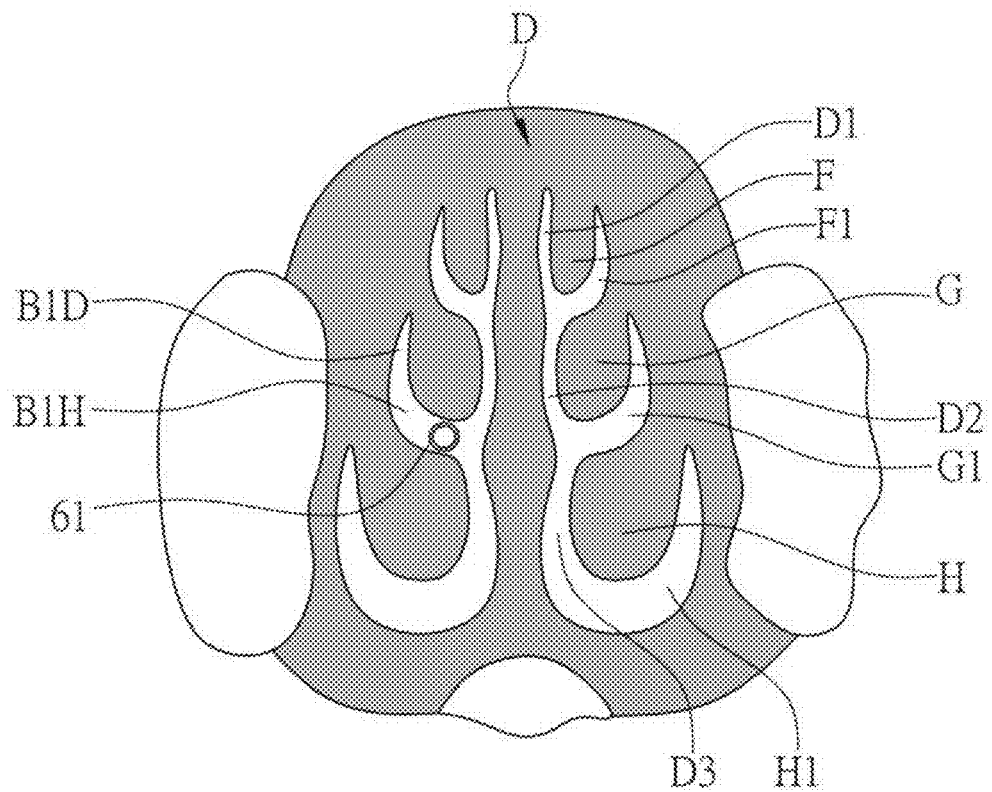
FIG. 16 is a coronal section view of posterior half of the nasal cavity, showing the high-pressure catheter disclosed in Taiwan Invention Patent No. 1542371 is only allowed to place in the horizontal section of middle nasal meatus.
Figure 17:
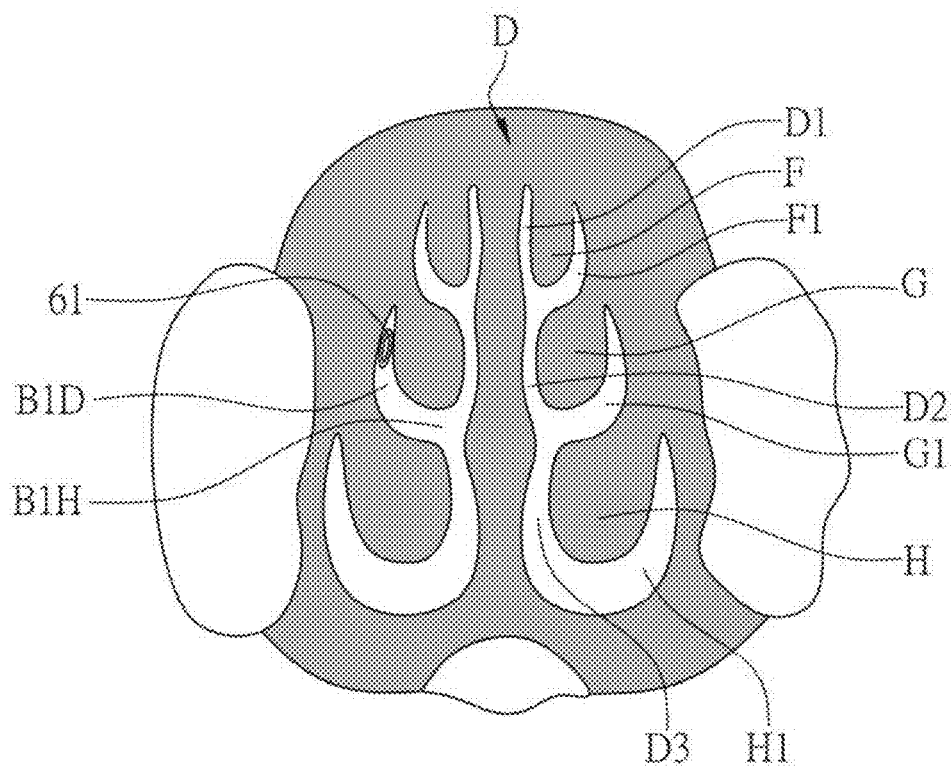
FIG. 17 is a coronal section view of posterior half of the nasal cavity, showing that the present invention of collapsible nasal ejecting catheter is able to insert into the descending section of the middle nasal meatus.
Figure 18:
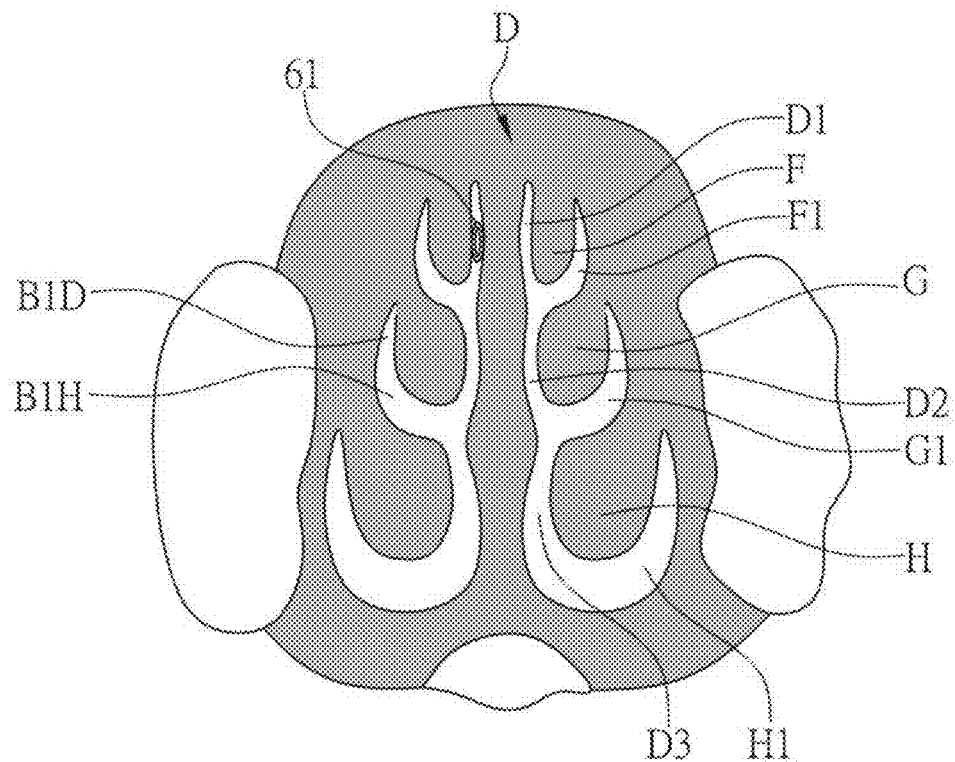
FIG. 18 is a coronal section view of posterior half of the nasal cavity, showing that the present invention of collapsible nasal ejecting catheter is able to insert in to the superior para-septal space.
Figure 19:
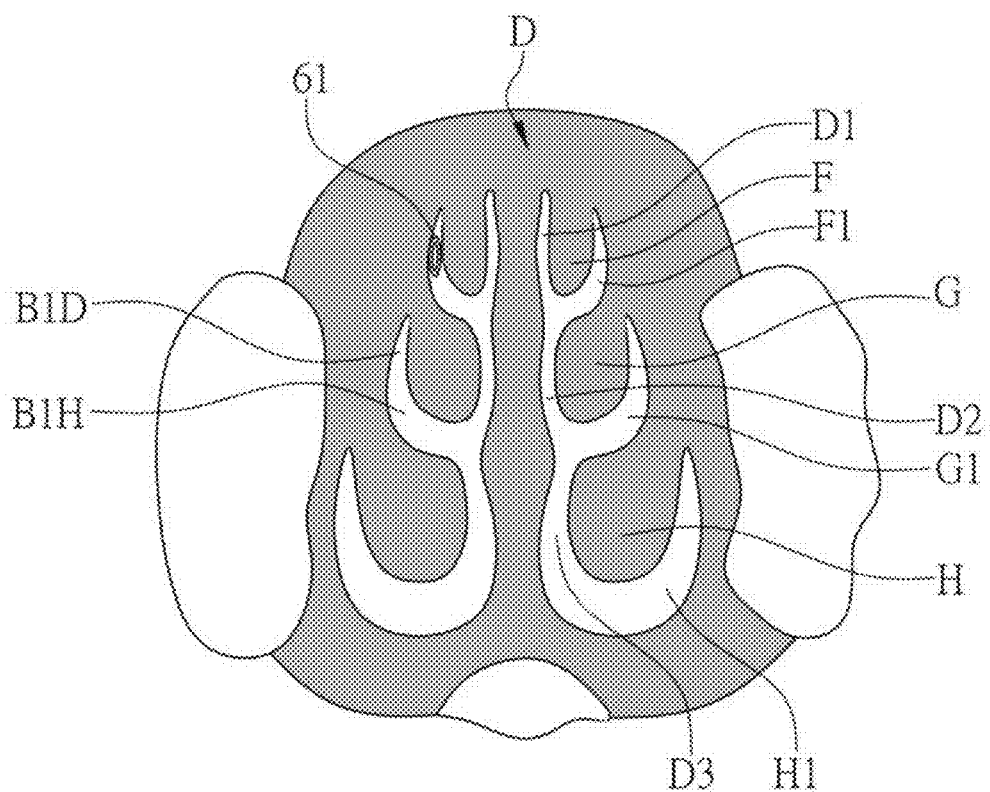
FIG. 19 is a coronal section view of posterior half of the nasal cavity, showing the present invention of collapsible nasal ejecting catheter is able to insert in to the superior nasal meatus.
Figure 20:
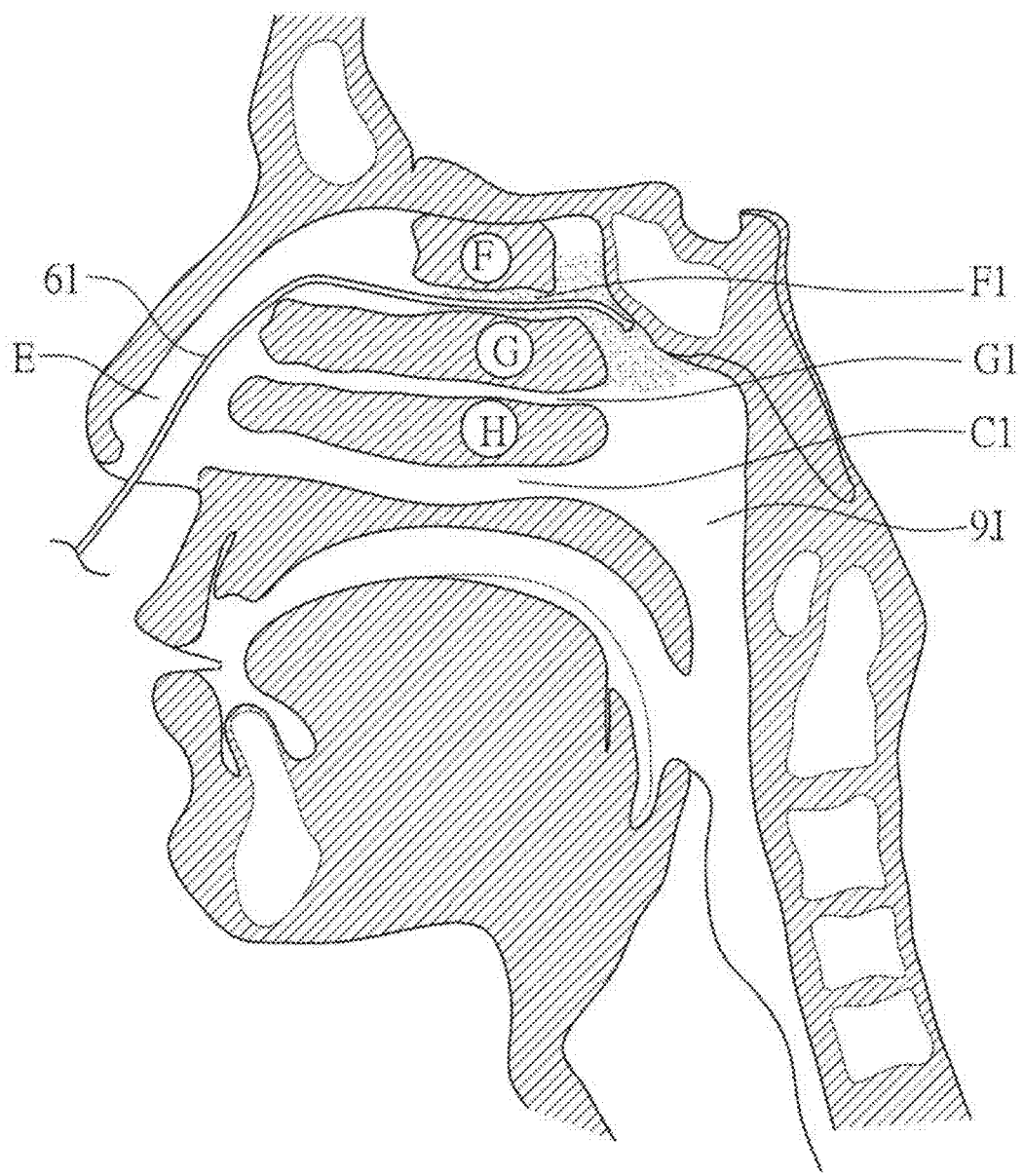
FIG. 20 is a sagittal section view of the human nasal cavity, showing that the present invention of collapsible nasal ejecting catheter is inserted into the nasopharynx through the superior nasal meatus for flushing.

Please refer to FIGS. 9, 10, 11, and 12, cross-sectional views of the flat closed distal end 611. The flat closed distal end 611 is produced by hot melt, ultrasonic welding, tip forming dies, or any other method. From the closed distal end to the normal circular appearance of the catheter, it is called the transitional segment TS. The transitional segment TS can be further divided into a flat closed segment FCS and an oval segment OS. Then, the oval section OS gradually transform to a normal segment NS with a circular appearance. The width of the transitional segment TS can be larger than, equal to, or smaller than the diameter of the catheter body. The oval segment OS also has a lumen 615, and the side-holes 613 may also be disposed. Please refer to FIGS. 10 and 12, the angle formed by the line (dashed line) between the flat closed distal end 611 to the normal circular portion is called transitional angle. Please refer to FIGS. 13, 14 and 15, cross-sectional views of the catheter near the flat closed distal end 611. FIG. 13 is a cross-sectional view of the b-b line of the flat closed segment FCS with flat appearance. FIG. 14 is a cross-sectional view of the c-c line of the oval segment OS with oval configuration. FIG. 15 is a cross-sectional view of the d-d line of the normal segment NS with circular appearance. Above description only indicates possible changes in the catheter shape, which does not necessarily represent the exact proportion.

The catheter is characterized by:
1. collapsibility;
2. flat closed distal end; and
3. transitional segment.

The first feature is collapsibility. The elastic catheter will be deformed when pressure is applied, and once the pressure is released, it will be restored to the original shape. The greater the pressure, the larger the deformity. However, with smaller outer diameter, harder material and the thicker catheter wall 614, the resistance to deformity is greater, and vice versa. The pressure required for complete collapse is greatly increased, so the half-collapsed lumen 615 has an optimal efficiency, and the half-collapsed lumen 615 is defined as collapsibility. The compression force exerts between catheter 61 and the nasal mucosa mutually, and the half-collapsed lumen 615 without causing pain is called the harmless collapse. In the field of otolaryngology, it is well known that gauze or packing device is used to pack the nasal cavity for hemostasis. The medical literatures suggest that the packing pressure should not be too high, but an exact value of pressure cannot be found. However, the exact data of the trachea, also classified as respiratory system, has been mentioned by some reports. These reports suggest that the cuff pressure of endotracheal tube should not exceed 30 mmHg=40.8 cmH2O. The main consideration is that the endotracheal tube should be used for several consecutive days or longer, if the pressure is too high, it is easy to cause complications such as tracheal necrosis, so we use this as a standard harmless pressure. For more than two years, we have been using high-pressure ejecting catheters for nasal flushing treatment. There are no problems with intolerable nasal pain or complications of nasal mucosal necrosis. We used a pressure gauge to measure the intraluminal pressure of the high-pressure ejecting catheter of the prior application during high-pressure injection. The result is that 1 to 4 atmospheres can even reach 5 atmospheres in a transient moment. Although this pressure does not exert directly to the nasal mucosa during the entire process of nasal flushing treatment, it can still prove that the tolerable pressure of the nasal mucosa in the nasal treatment is much larger than the tolerable pressure of (40.8 cmH2O) of the trachea. Because the width of normal middle nasal meatus and inferior nasal meatus is about 3 mm, the outer diameter of 3 mm is set as the standard catheter size, and then the standard size catheter of various hardness materials is compressed at the harmless pressure to test the thickness of half-collapsed lumen 615, so that the maximum wall thickness of the catheter with harmless collapse can be obtained. The following are the maximum harmless collapse thickness of the catheter wall 614 tested in different hardness obtained from the experiment: the wall thickness of polyether block amide (Pebax) 4033 (90 Shore A) is about 0.40 mm; the wall thickness of Pebax 3533 (80~82 Shore A) is about 0.45 mm; the wall thickness of Pebax 2533 (74~77 Shore A) is about 0.50 mm; the wall thickness of silicone with 60 Shore A is about 0.55 mm; the wall thickness of silicone with 50 Shore A is about 0.60 mm.

Because there are many materials that meet the requirements, it is impossible to test them all. The above are common materials to test the maximum wall thickness of various hardness under collapsed condition, which are not necessarily those for commercialization in the future. The outer diameter of the conventional nasal flushing catheter cannot be larger than the maximum transverse diameter of the nasal passage of 3 mm, but the present invention is a collapsible catheter with a flat closed distal end 611, which is not limited by 3 mm, and may be up to 5 mm or even larger. If the outer diameter is larger, the maximum wall thickness for harmless collapse will be increased.

Since the purpose of the present invention is to function as a microcatheter (outer diameter less than 1 mm) for insertion into the deepest narrow recess, the thickness of the flat closed distal end 611 is not larger than 1 mm, preferably not larger than 0.9 mm. Besides, it is difficult for complete collapse, so the thickness of the catheter wall 614 is set to be not larger than 0.45 mm.

The collapsible nasal ejecting catheter is completely different from the common catheter. The collapsibility is a special design of the nasal ejecting catheter 6 for entering the narrow slit-like space. Because after the entrance into the narrow slit-like space, the collapsed nasal ejecting catheter has to restore to the original round shape when ejecting spouts by forceful injection. Therefore, the collapse and the forceful injection must be considered together. Except those catheters directly placed into the body by surgical operation, all the catheters inserted into the body are designed to have a smooth surface and a uniform size (or a tapered end), and have some degree of flexibility to accommodate the human body space. However, in normal condition, it is absolutely not allowed to be collapsed, because it will result in increased size in one dimension, a different outer diameter and a rough surface. It violates the principle of smooth surface and uniform size (or tapered end). Either the insertion to or removal from the body, it is traumatic to surrounding tissue, which completely violates the general principle of minimum injury. In addition, the function of the ordinary catheters are drainage (the fluid flows from the human body space to lumen 615 and then to outside of the body spontaneously), suction (the fluid flows from the human body space to lumen 615 and then to outside of the body by force), or low-pressure fluid delivery (the fluid flows from the lumen 615 to the human space in a low-pressure state); the function of drainage, suction or low-pressure fluid delivery depend on the cross-sectional area of the lumen, so that collapse of the catheter wall 614 will impedes the drainage, suction or low-pressure fluid delivery, in violation of the general design principle of catheter. In addition, except the nasal cavity, the other spaces of the human body are closed spaces, and the ordinary catheters are used in such closed spaces. It cannot be designed with a pressurized ejecting function (with a small total area of the side-holes), because the strong spouts may cause back flow of the infected substances into the bloodstream to cause sepsis (the spaces required drainage and suction space are usually infected). It may also cause rupture of outer wall of the space due to sudden elevation of pressure. The collapsible catheter has to be restored to the original shape by forceful injection to eject strong spouts; therefore, it is difficult to control the pressure during forceful injection. Considering the above side effects of the collapsible catheter, it cannot be used in a closed space, but only suitable for nasal flushing treatment, which is different from other catheters.

Figure 2:
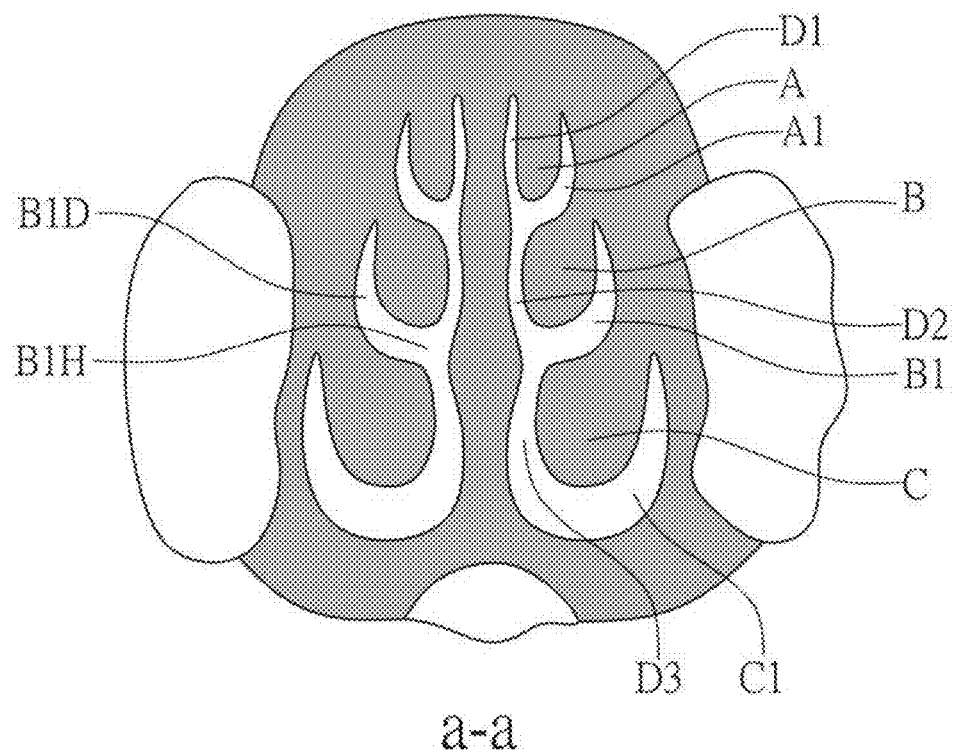
FIG. 2 is a coronal section view, showing the posterior half of nasal cavity along the a-a line in FIG. 1.
Figure 3:
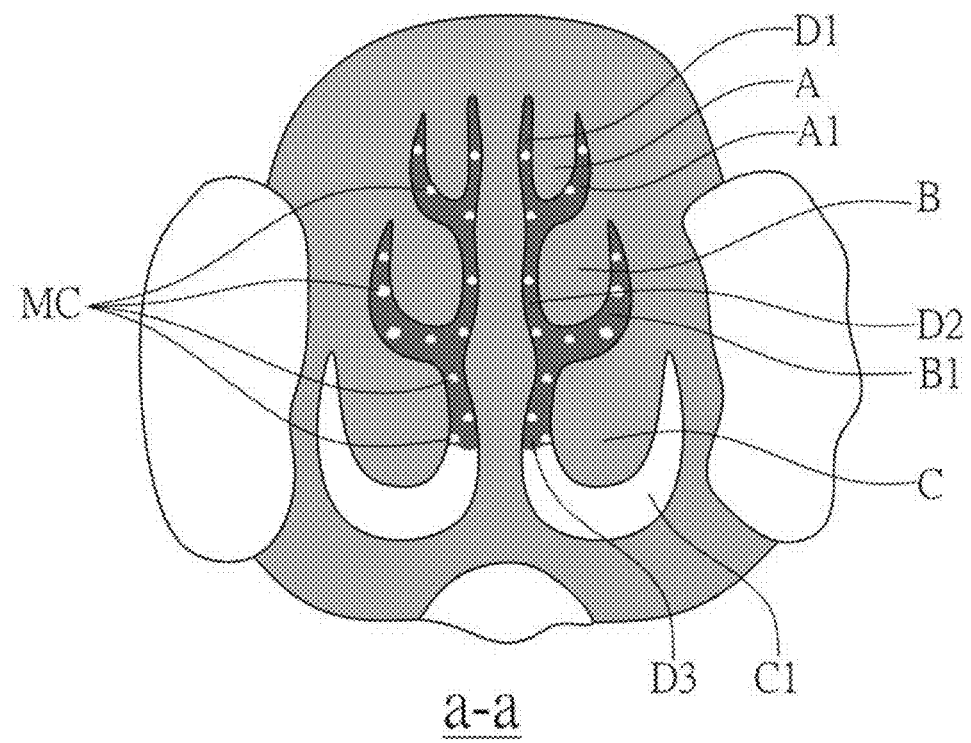
FIG. 3 is a coronal section view of the posterior half of the nasal cavity, showing the accumulation of mucus and booger extended from superior para-septal space, superior nasal meatus and middle nasal meatus to inferior para-septal space in a patient of chronic sinusitis.
Figure 4:
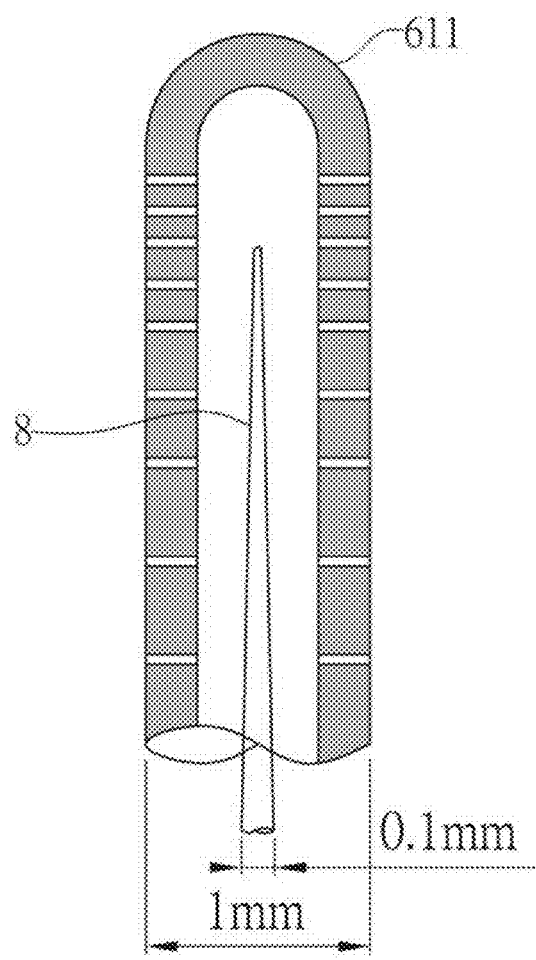
FIG. 4 is a cross-sectional view of a nasal flushing device disclosed in Taiwan Invention Patent No. I542371.
Figure 5:
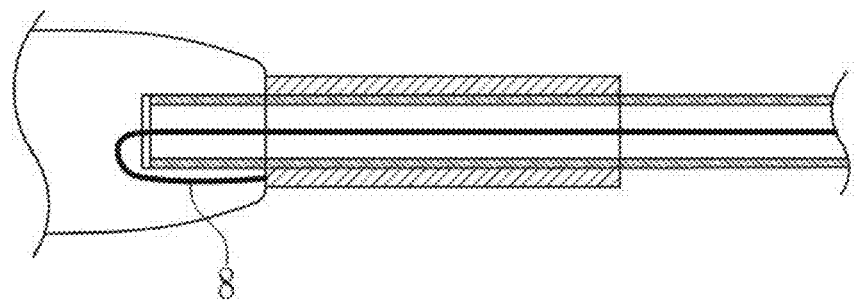
FIG. 5 is a partial cross-sectional view of the nasal flushing catheter disclosed in Taiwan Invention Patent No. I542371, showing the connection of a connector and the catheter body as well as the safety design of the stylet.

The second feature is the flat closed distal end 611. Please refer to FIGS. 9, 10, 11 and 12. Circular or flat, the circular shape is equal size in two dimensions, while the flat shape is different size in two dimensions; therefore, if not circular, it belongs to flat. In general, the different size in two dimensions is not good for insertion into or removal from the body, in violation of the principle of uniformity of the size or the tapered end of the catheter design. However, the nasal cavity of the human body is a front to back slit-like space, narrower in upper and wider in lower (Please refer to FIG. 2); the widths of these spaces are measured in mm, while the heights are measured in cm. Because the two dimensions of nasal cavity are so different, which is totally different from other space in the human body, the circular design of the catheter is unnecessary, and the distal end is not necessarily smaller than the shaft of catheter. In contrast, the flat closed distal end 611 is more favorable for entering the slit-like space, and the description is as follows:

The conventional round-ended catheter can only enter a space larger than its outer diameter, but once the collapsed oval short diameter (SD) of the present invention is smaller than the width of the slit-like space, no matter how long the collapsed oval long diameter (LD), the collapsed catheter can pass through this narrow slit-like space. The cross section of the catheter is circular, and the outer circumference is equal to the outer diameter times Pi, the equation is OC=OD*3.14; the inner circumference is equal to the inner diameter times Pi, and the equation is IC=ID*3.14.

Please refer to FIGS. 13, 14 and 15; the first embodiment is a catheter with 2 mm outer diameter, 1.5 mm inner diameter, and 0.25 mm wall thickness 614. The flat closed distal end 611 or the width (W) of the complete collapsed catheter is equal to the total thickness of both catheter wall (t) plus the circumference width of the collapsed inner lumen, the equation is W=2t+ID*3.14/2, the value is W=0.5+1.5*3.14/2=2.855 mm, the width is much larger than the 2 mm diameter, but the thickness is only 0.25 mm×2=0.5 mm, which can pass through a 0.5 mm narrow space. However, it is not easy for complete collapse, suppose half collapse of the catheter to become an oval shape, a 2 mm catheter can pass through a narrow space of 1.25 mm=2−(1.5/2) mm.

The second embodiment is a catheter with 3 mm outer diameter, 2.4 mm inner diameter and 0.3 mm catheter wall 614. The flat closed end 611 or the width (W) of the complete collapsed catheter is 0.6+2.4*3.14/2=4.368 mm, still much larger than 3 mm in diameter, but only 0.3 mm×2=0.6 mm in thickness, can pass through a 0.6 mm narrow space. However, it is not easy for complete collapse, suppose 3/4 collapse of the catheter to become an oval shape, a 3 mm catheter would be able to pass through a narrow space of 1.2 mm=3−(2.4*3/4) mm.

The third embodiment is a catheter with 1.5 mm outer diameter, 1.2 mm inner diameter and 0.15 mm catheter wall 614. The flat closed distal end 611 or the width (W) of the complete collapsed catheter is 0.3+1.2*3.14/2=2.184 mm, also much larger than 1.5 mm in diameter, but the thickness is only 0.15×2=0.3 mm, which can pass through a narrow space of 0.3 mm. However, it is not easy for complete collapse, suppose 3/4 collapse of the catheter to become an oval shape, a 3 mm catheter would be able to pass through a narrow space of 0.6 mm=1.5−0.9 mm.

All three embodiments prove that the flat closed distal end 611 is more favorable for entering the slit-like space, but the flat closed or oval shape violates the principle of uniform size or tapered end of the catheter design, and is only suitable for the nasal cavity.

The flat closed distal end can be produced by hot melt, ultrasonic welding, tip forming dies or any other method. From flat to round shape, there must have an oval transitional segment TS. The tip forming dies can manufacture different shapes, and the width of the end can be larger than, equal to, or smaller than the diameter of the catheter shaft, and the purpose can be obtained by other manufacturing methods.

The inventors are deeply sympathetic to the suffering of patients with chronic sinusitis, who cannot have effective treatment. Due to the thorough study of the character of elastic catheter, we found eventually that the collapsibility and the flat closed distal end 611 of catheter, which were abandoned by the person skilled in the art, are favorable for nasal flushing treatment.

The different functions created by the special design of the present invention can be illustrated as follows:

The average initial velocity ($V_0$) of side-holes 613 spouts can determine the average vertical height h, hence, its equation is as the following: $V_0=gt$ or $t=V_0/g$, wherein, g is the gravitational constant 9.8 m/sec², t is the time reaching the vertical apex. The maximum vertical apex h, can be determined by the equation $h=1/2(gt^2)$, plugging $t=V_0/g$, and $h=1/2(g)(V_0/g)^2=V_0^2/2g$ or $V_0^2=2gh$; furthermore, the average initial velocity ($V_0$) of side-holes 613 spout can be determined by the injection rate (IR) and the total area of side-holes (TA), the equation is as following: $V_0=IR/TA$ when applies to the function $V_0^2=2gh$, and then will get $(IR/TA)^2=2gh$. Therefore, the vertical height of the spouts is proportional to the square of the injection rate. Although the injection rate is related to the applied pressure, it is further limited by the flow rate in the lumen, and the flow rate in the lumen is limited by the cross-sectional area of the lumen 615 and is proportional to the cross-sectional area of the lumen 615. The vertical height of the spouts is eventually proportional to the square of the cross-sectional area of the lumen 615.

In the first embodiment, the conventional catheter can only use an outer diameter of 1.25 mm through a narrow space of 1.25 mm, but the outer diameter of the present invention can be 2 mm supposed that the outer diameter, the inner diameter and the thickness of the catheter wall 614 have the same ratio, the inner diameter of the 2 mm catheter is 1.6 times larger than the 1.25 mm catheter, the cross-sectional area is 2.56 times larger, the flow rate and injection rate are increased by 2.56 times, and the vertical height of the spouts is increased by 6.55 times.

In the second embodiment, similarly, the conventional catheter can only use an outer diameter of 1.2 mm through a narrow space of 1.2 mm, but the outer diameter of the present invention can be 3 mm. Supposed that the outer diameter, the inner diameter of the catheter, and the thickness of the catheter wall 614 also have the same ratio, the inner diameter of the 3 mm catheter is 2.5 times larger than the 1.2 mm catheter, the cross-sectional area is 6.25 times larger, and the vertical height of the spouts is increased by 39 times.

In the third embodiment, the conventional catheter can only use an outer diameter of 0.6 mm through a narrow space of 0.6 mm, but the outer diameter of the present invention can be 1.5 mm. Supposed that the outer diameter, inner diameter, and wall thickness 614 of the catheter also have the same ratio. The inner diameter of the 1.5 mm catheter is 2.5 times larger than the 0.6 mm catheter, the cross-sectional area is 6.25 times larger, and the vertical height of the spouts is 39 times larger. Because the flushing efficacy is directly related to the vertical height of the spout, either 39 times or 6.55 times is a huge difference, and it will greatly improve the flushing efficiency.

In a narrow space, the collapsed catheter may not fully be restored to circular shape, but even so, the cross-sectional area of the collapsible lumen is still larger than a conventional catheter, which will be explained below:

The circumference equation is $C=3.14*R$, wherein C is the circumference and R is the diameter of the circle. The circle area equation is $S=0.785*R2$. The oval circumference equation is $L=2\pi b+4(a-b)$, wherein 'a' is the radius of long axis and 'b' is the radius of short axis. This formula can be replaced by $a=(L+4b-2\pi b)/4$, and the oval circumference formula is $S=\pi ab$, wherein $\pi$ is the Pi 3.14.

In the first embodiment, the outer diameter of the present invention is 2 mm, the inner diameter is 1.5 mm, the inner circumferential length L is 4.71 mm, and then compressed to an oval with short axis outer diameter SD of 1.25 mm in a narrow space, wherein the diameter of the short axis lumen is 0.75 mm, the radius of short-axis lumen is b=0.375 mm, then the radius of long-axis lumen is $a=(L+4b-2\pi b)/4=(4.71+1.5-2.355)/4=1.34$ mm, the long axis outer diameter LD is (1.34 mm+0.25 mm)*2=3.18 mm, and the cross-sectional area of the oval lumen is $S=3.14*a*b=3.14*1.34*0.375=1.57785$ mm² If the conventional catheter with an outer diameter of 1.25 mm corresponding to the present invention has the same ratio of outer diameter and catheter wall, and its lumen diameter is 1.25 mm*0.75=0.9375 mm, and the cross-sectional area of lumen is $S=0.9375*0.9375*0.785=0.6899$ mm². By comparison, the ratio of the cross-sectional area of the present invention to the conventional catheter is 1.57785/0.6899=2.287 times, and the height of the spouts can still reach 2.287*2.287=5.23 times.

In the second embodiment, the outer diameter of the present invention is 3 mm, the inner diameter of lumen is 2.4 mm, the inner circumferential length L=3.14*2.4=7.536 mm, and then compressed to an oval with short axis outer diameter SD of 1.2 mm in a narrow space (the diameter of short axis lumen is 0.6 mm, and the radius of short axis lumen is b=0.3 mm), and the radius of the long axis lumen is $a=(L+4b-2\pi b)/4=(7.536+1.2-2*3.14*0.3)/4=1.713$ mm, the long axis outer diameter LD is (1.713 mm+0.3 mm)*2=4.026 mm, and the cross sectional area of the oval lumen is $S=3.14*a*b=3.14*a*b=3.14*1.713*0.3=1.6136$ mm² If the conventional catheter with an outer diameter of 1.2 mm corresponding to the present invention has the same ratio of outer diameter and catheter wall, and its lumen diameter is 1.2 mm*0.8=0.96 mm, and the cross-sectional area of lumen is $S=0.96*0.96*0.785=0.7234$ mm² By comparison, the ratio of the cross-sectional area of the present invention to the conventional catheter is 1.713/0.7234=2.23 times, and the height of the spouts can still reach 2.23*2.23=4.97 times.

In the third embodiment, the outer diameter of the present invention is 1.5 mm, the inner diameter of lumen is 1.2 mm, the inner circumferential length is 3.768 mm, and then compressed to an oval with short axis outer diameter SD of 0.6 mm in a narrow space (the inner diameter of short axis is 0.3 mm, and the radius of short axis lumen is b=0.15 mm), and the radius of the long axis lumen is $a=(L+4b-2\pi b)/4=(3.768+4*0.15-2*3.14*0.15)/4=0.8565$ mm, the long axis outer diameter LD is (0.865 mm+0.15 mm)*2=2.03 mm, and the cross sectional area of the oval lumen is $S=3.14*a*b=3.14*0.8565*0.15=0.4034$ mm² If the conventional catheter with an outer diameter of 0.6 mm corresponding to the present invention has the same ratio of outer diameter and catheter wall, and its lumen diameter is 0.6 mm*0.8=0.48 mm, and the cross-sectional area of lumen is $S=0.48*0.48*0.785=0.180864$ mm² By comparison, the ratio of the cross-sectional area of the present invention to the conventional catheter is 0.4034/0.180864=2.23 times, and the height of the spouts can still reach 2.23*2.23=4.97 times.

Even the collapsed portion of the present invention does not expand during forceful injection; the height of the spouts can still reach 4.97 times. With some degree of expansion, the spout would be stronger. Further, this is only that happens in the deep narrow recess which only accounts for a part of 5 cm length of the catheter within nasal cavity proper. Further, the catheter is about 15 cm long, and the collapsed proportion is smaller, so the influence of the collapsed portion on the lumen flow rate would be smaller, and the height of the spouts should be stronger.

Figure 10:
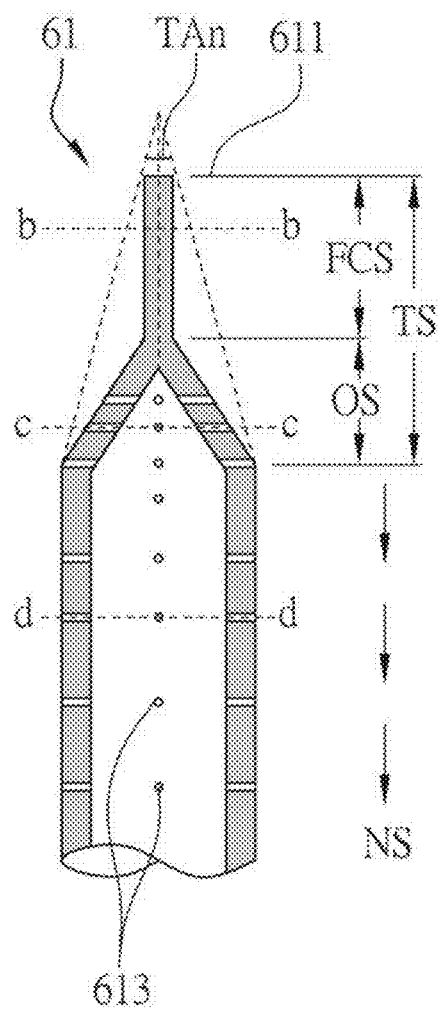
FIG. 10 is a partial cross-sectional view, showing the side view of the flat closed distal end of the present invention.
Figure 9:
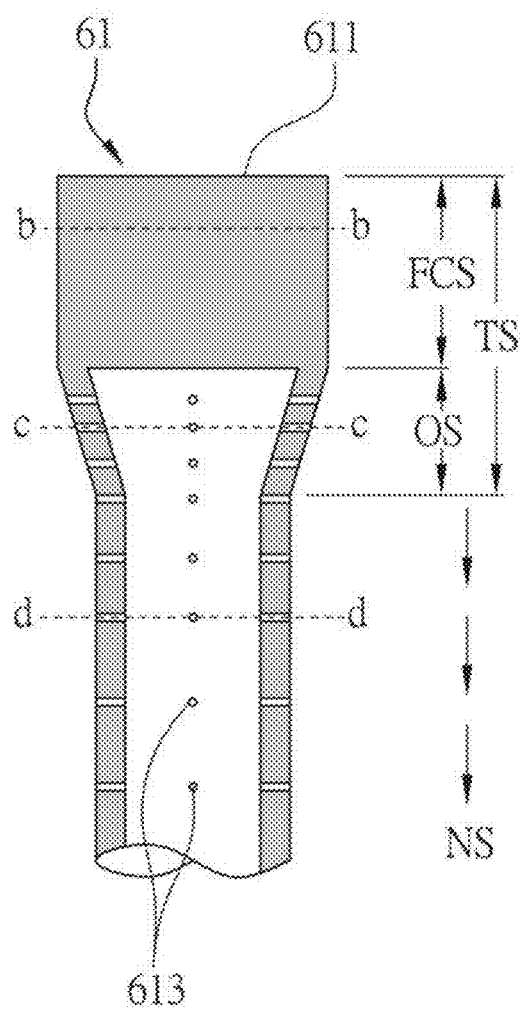
FIG. 9 is a partial cross-sectional view, showing the front view of the flat closed distal end of the present invention.
Figure 12:
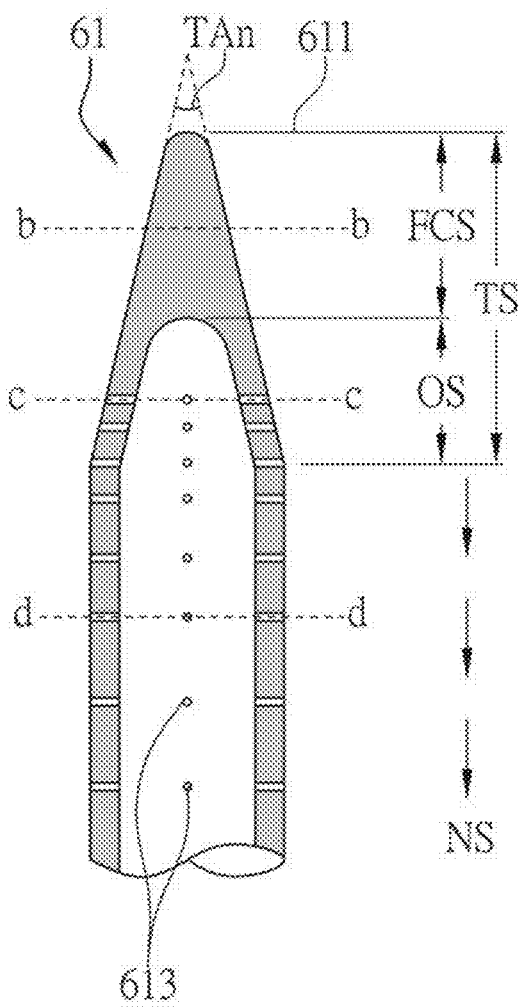
FIG. 12 is a partial cross-sectional view, showing the side view of the flat closed distal end of the present invention produced by the tip forming dies.
Figure 11:
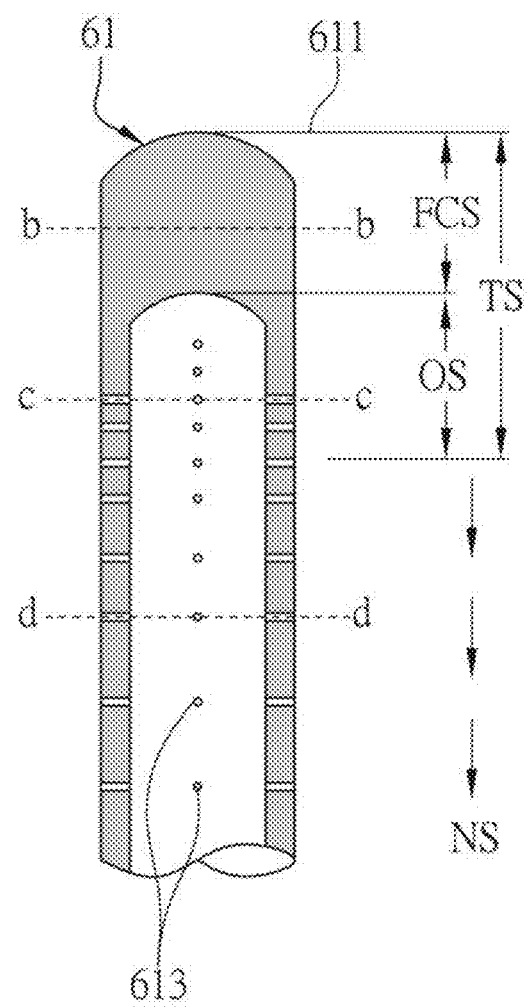
FIG. 11 is a partial cross-sectional view, showing the front view of the flat closed distal end of the present invention produced by the tip forming dies.

The third feature is transitional segment. Please refer to FIGS. 10 and 12, a transitional segment TS is the segment from the flat closed distal end 611 to the normal circular appearance of the catheter, and the transitional segment TS can be further divided into a flat closed segment FCS and an oval segment OS. The angle between the lines (dashed line) from the flat closed distal end to the normal circular appearance is called the transitional angle TAn. Please refer to FIGS. 9 and 11; the front-side width of the transitional segment TS may be larger than, equal to, or less than the diameter of the catheter, but its side thickness is less than the catheter diameter. If the flat closed distal end 611 enters the narrow space, the transitional segment TS can induce the catheter to collapse along the direction of the oval segment OS. In addition, the transitional segment TS is also like a guidewire to guide the catheter in the deep direction. The longer the transitional segment TS, the smaller the transitional angle TAn, and the better the guiding function. However, this is not for all the case. The flat closed segment FCS shown in FIGS. 9 and 10 is produced by non-mold method, which is to flatten the distal end of the catheter and then heated in various fusion methods. The dashed line represents the original lumen, while the oval segment OS is formed naturally, so its length cannot be control. The flat closed segment FCS must be flattened to less than twice the wall thickness of the catheter to ensure the purpose of complete closure, so that such flat closed segment FCS is easy to deform and is hard to maintain a smooth flat surface, and the longer the FCS, the worst the deformity. It is easy to get stuck in the narrow space for an uneven closed end. In addition, the transitional segment TS must have a gradual change of softness to function as a guidewire to guide the catheter, but the flat closed segment FCS has the same thickness and does not have a gradual change of softness. If the transitional segment TS is too long, it cannot function as the wire, so longer is not necessarily better. Please refer to FIGS. 11 and 12, the transitional segment TS includes a flat closed segment FCS and an oval segment OS which are produced by tip forming dies and have a structure of perfect tapered end, which meets the requirements of the gradual change of softness of a guidewire, therefore, the longer transitional segment TS is, the better the guiding function. But the longer the transitional segment TS, the more difficult to produce by the tip forming dies. In general, the ideal and reality must be compromised. The length of the transitional segment TS is not more than 30 mm in general, preferably 25 mm or 20 mm. If the transitional segment TS is too short, the guiding function is not good, so it is not less than 2 mm in general. The larger the transitional angle TAn, the less likely to be collapsed, so the transitional angle TAn is not more than 45 degrees, preferably 30 degrees, 15 degrees or 10 degrees. The ratio of width to thickness of the flat closed distal end 611 is called flat ratio, the width is measured at the maximum circular arc. The greater the flat ratio, the better the directionality, and the better the collapse leading function in a single direction of the oval segment OS and the normal segment NS. The round end of the conventional catheter has a flat ratio of 1, can be arbitrarily rotated, has the worst directionality, and has the worst function of collapse leading of the catheter, but is most suitable for suction, drainage or delivery of fluid. The flat ratio of the catheter is not less than 1.5 in general, preferably 3, 4, 5 or 6, and the larger the better.

In conclusion, the present invention allows the flat closed distal end to enter a narrow space, and the transitional segment TS to guide the advancing direction and the collapse of the catheter, so that the entire catheter can enter the desired narrow space. In summary, the special design of the present invention will greatly improve the flushing efficiency.

Other advantages and considerations of the present invention: Since the nasal flushing treatment is a daily home remedy, the equipment must be reused, and the present invention can adopt a larger catheter as described above, by using materials with appropriate hardness and appropriate thickness of catheter wall 614 to achieve better controllability. Therefore, it can reach the narrow space without a retained stylet, and there is no risk of protruding of stylet out of the catheter to hurt the patient or release of heavy metal due to repeated use.

Due to the created properties of collapsibility, flat closed distal end 611 and transitional segment TS, the present catheter is easy to reach the narrowest roof of the superior nasal meatus and the middle nasal meatus, therefore, it is very important to avoid getting into the sinus. For example, in the third embodiment, a 1.5 mm catheter can be 3/4-collapsed to become a catheter with 0.6 mm short-axis outer diameter SD and 2.03 mm long-axis outer diameter LD, which can pass through a 0.6 mm narrow space which is smaller than 1 mm sinus orifice, but the width (2.184 mm) of the closed distal end 611 and the collapsed oval long axis diameter LD (2.03 mm) are much larger than 1 mm, and it is impossible to pass through a 1 mm circular sinus orifice, so that it is enough to avoid accidental entry into the sinus. On the other hand, if a conventional catheter can enter a narrow space of 1 mm, its round closed end must be less than 1 mm, so it may accidentally enter the sinus, which is not the purpose of flushing the nasal cavity, and the consequences are as follows.

Using catheter to enter paranasal sinuses followed by irrigation of fluid is a method of surgical treatment of sinusitis by physician. This surgical operation requires an endoscopic and fluoroscopic monitoring for confirm the entry into the sinus. This is a very professional surgical technique. Physicians must undergo special training and entering the sinus is not easy. Once the catheter enters this sinus, the mucus and inflammatory substances in the sinus must be aspirated immediately, otherwise there is a risk of failure of the operation, so that the catheter must have good suction function. Suction denotes fluid flows from the outside to inside of the catheter by force. The suction function refers to the flow rate of fluid flowing from the outside to inside of the catheter. The flow rate is determined by the size, number and total area of the side-holes, and finally is proportional to the total area of the side-holes. For suction of the sticky mucus or particulate material, large size and small number of side-holes is better than small size and large number of side-holes, therefore, the suction catheter must have a large size side-hole and a large total area of side-hole, the design principle of the side-hole is totally different from the present nasal ejecting catheter 6 (the side-holes are small in size and large in number, because the strength of spouts is inversely proportional to the square of total area of side-holes). On the contrary, during flushing treatment using the present catheter by patient, the location of the catheter is unknown, but must follow by forceful injection of flushing fluid to eject strong spouts. Since the nasal cavity is an open space, no matter how much fluid, it will be flow out immediately. However, if the catheter accidentally enters the sinus, because the sinus is a closed space, and the outlet has been plugged by the catheter, a large amount of injected fluid cannot be discharged, which may cause acute sinusitis. Further, the high-pressure spouts may cause back flow of infected substances into the bloodstream to cause sepsis, and may even cause rupture of sinus wall by sudden elevation of pressure, spreading to the adjacent meninges to cause meningitis.

Therefore, the conventional round closed end catheter may cause accidental entry into the sinuses and serious complications, which is a dangerous design. The catheter provider must take the responsibility; this is why our prior application has not been commercialized. In order to avoid accidental entry into the sinus, the width of the flat closed segment FCS or the oval long axis LD of the oval segment OS of the present invention is not less than 1 mm, preferably not less than 1.2 mm, or 1.5 mm, or 2 mm, or more. After the flat closed segment FCS enters the narrow space, the oval segment OS will induce the collapse of the circular catheter to enter the narrow space. If the maximum width of the oval transitional segment TS is larger than 1 mm, the width after collapse is much larger than 1 mm, and it could avoid entering the sinus through the 1 mm sinus orifice.

Although the material of the catheter can reach 90-100 Shore A, the harder material must have thinner maximum harmless collapse thickness of catheter wall. Accordingly, due to the collapsibility, the flat closed distal end 611 would not be too hard; a smooth round tip can be produced, and may not hurt the patient.

Therefore, selecting appropriate collapsible material and catheter wall 614 and following the design concept of the present invention can achieve the purpose of flushing the narrow space of nasal cavity by a large catheter.

Because the hand-made prior catheter has been tried by the inventor before filing, it has been more than two years. Furthermore, the present invention has been tested for nearly half a year, so we have the opportunity to compare the differences between different catheters and also realize the patient's suffering. Patient can accept the troublesome daily nasal flushing treatment as long as the symptoms are sufficiently improved.

Please refer to FIGS. 16~19; the nasal cavity is divided into three slightly curved slit-like passages by three plate-like structures. The three plate-like structures are the superior turbinate F, the middle turbinate G, and the inferior turbinate H. The three passages are the superior nasal meatus F1, the middle nasal meatus G1 and the inferior nasal meatus H1. Because the nasal cavity is symmetrical, the space close to midline of the nasal cavity is called the para-septal space D, wherein the para-septal space can be divided into the superior para-septal space D1, the middle para-septal space D2, and the inferior para-septal space D3. Please refer to FIGS. 12~15, coronal section views of posterior half of the nasal cavity, showing that all nasal meatus F1, G1, and H1 are narrow in upper and wider in lower. The middle nasal meatus is further divided into a 2 in descending section BM (mucus from above), and a 1 cm horizontal section B1H. The narrowing of all the air passages are due to repeated coating of crust layer by layer over the years.

Since the prior high-pressure catheter body 61 with large outer diameter capable of ejecting strong spouts, can only be placed in the wide horizontal section B1H (shown in FIG. 16), because the spouts cannot reach the descending section B1D, so the effect is not good. Although using the prior small catheter with retained stylet can reach the descending section, the spouts are weak and the efficiency is low. Further the stylet may protrude from the catheter to hurt the patient. On the other hand, the collapsible catheter body 61 of the present invention having a similar size to the prior high-pressure catheter, can be placed in the narrow descending section BM (shown in FIG. 17), and the best flushing efficacy can be obtained as explained above. Because the present invention has the advantages of the fineness of the microcatheter and the controllability of the large catheter, during operation, under the guidance of the flat closed distal end 611, if the catheter advances upward and backward closely along the nasal septum, because of collapsibility, it can arrive at the superior para-septal space D1 (see FIG. 18) or the adjacent superior nasal meatus F1 (see FIG. 19). If it advances slightly upward, outward, and backward, it can easily reach the narrow descending section BM of the middle nasal meatus G1 (FIG. 13). It is indeed possible to flush the small slit-like space using a large catheter.

Even if the prior high-pressure catheter body 61 can only be placed at inferior portion of the descending section B1D, and the strong and thin spouts can be ejected upward along the slit, but the perpendicular vector of paralleling spouts is almost zero, and the spouts parallel to the slit cannot peel out the crust stuck to the 2 cm descending section B1D, it only rinse the crust. Moreover, the narrow space becomes completely blocked by the swollen crust soaked with flushing fluid, and the symptoms aggravate. The front to back unidirectional spouts of conventional nasal flushing device also have zero perpendicular vector due to longer distance, also cannot peel off the crust stuck to the 5 cm long nasal cavity proper, also causes aggravation of symptoms. Such patients may be those failed in nasal flushing treatment and suggested for operation by medical experts.

On the contrary, the collapsible catheter body 61 of the present invention can be placed at the upper narrow descending section B1D, because the strong spouts are directly ejected to the adjacent crust perpendicularly, which thickness is measured in mm, the effect is obvious. Similarly, the collapsible catheter body 61 of the present invention is placed in the superior para-septal space D1 (see FIG. 18) and superior nasal meatus F1 (see FIG. 19), can also perpendicularly eject strong spouts to adjacent crusts measured in mm. Therefore, it is more effective than the prior high-pressure catheter which can only be placed in the middle para-septal space D2 or inferior para-septal space D3.

Please refer to FIGS. 16~20, the superior nasal meatus F1 is narrower, the mucus is easier to cause obstruction, and the air cannot pass through. The mucus remains liquid state due to lack of drying effect, and it is easy to flow back to the junction of superior nasal meatus F1 and the nasopharynx J. In contrast, the mucus of the middle nasal meatus G1 also flows into the nasopharynx, but the middle nasal meatus G1 is wider than the superior nasal meatus F1, and the mucus mostly flows downward to become a thin layer, which is easily dried by the respiratory air into a solid crust, so only a small part of mucus flows to the nasopharynx J. Therefore, the mucus that flows back to the nasopharynx J mainly comes from the superior nasal meatus F1. Hence, the best method of flushing mucus in nasopharynx is direct flushing with strong spouts by a catheter through superior meatus to the roof of nasopharynx, however, there is a sphenoid sinus at there, only the present invention can achieve the purpose and avoid accidental insertion into the sphenoid sinus.

Through the description of the above embodiments, it can be understood that the collapsible nasal ejecting catheter 6 of the present invention indeed have the following advantages: due to feature of the flat closed distal end 611, the transitional segment TS and the collapsibility of the catheter body 61, the larger catheter can insert deeply within the narrow flushing targets, can eject much stronger or more number of thin and long spouts for better flushing effect, and avoid the risk of accidental entry into the sinuses. It also can omit the necessity to perform computed tomography for measuring the width of the middle nasal meatus and the superior nasal meatus; it is possible to apply all the patients in two sizes or even one size of catheter, which is truly effective and convenient.

The collapsible nasal ejecting catheter 6 of the present invention can overcome the disadvantages of incomplete flushing of deep recess of the nasal cavity of the prior nasal flushing catheter, so that it can improve the symptoms of patients with chronic sinusitis, and reduce discomfort during operation. Meanwhile, it is also convenient for the patient in travelling.

The above descriptions are only explanations according to the preferred embodiments, and should not limit the scope the present invention. It is to be understood that many other possible modifications and variations can be made without departing from the spirit and scope of the invention as hereinafter claimed.

What is claimed is:

1. A collapsible nasal ejecting catheter which can be adapted to connect to a syringe for nasal flushing treatment, comprising:
   - a catheter body and a connector, the said catheter body including a flat closed distal end, a transitional segment comprising a flat closed segment and a lumen containing an oval segment, a circular normal segment and an open end on an opposite side of the flat closed distal end, and
   - multiple side-holes near the closed flat distal end; the said catheter body being made of soft and elastic material so that the catheter can be inserted into a slit space smaller than a diameter of the circular normal segment.

2. The collapsible nasal ejecting catheter as claimed in claim 1, wherein a hardness of the catheter is below 80 Shore A, and a wall thickness of the catheter is not larger than 0.45 mm.

3. The collapsible nasal ejecting catheter as claimed in claim 1, wherein a hardness of the catheter is between 80 and 90 Shore A, and a wall thickness of the catheter is not larger than 0.40 mm.

4. The collapsible nasal ejecting catheter as claimed in claim 1, wherein a hardness of the catheter is above 90 Shore A, and a wall thickness of the catheter is not larger than 0.35 mm.

* * * * *